United States Patent [19]

Hardison et al.

[11] 4,404,857

[45] Sep. 20, 1983

[54] SEAM TESTER

[75] Inventors: Leslie C. Hardison, Barrington; Kenneth A. Sandstrom, Prospect Heights, both of Ill.

[73] Assignee: National Seal Company, Palatine, Ill.

[21] Appl. No.: 303,215

[22] Filed: Sep. 18, 1981

[51] Int. Cl.³ .............................................. G01N 3/08
[52] U.S. Cl. ....................................... 73/827; 73/838
[58] Field of Search ................. 73/827, 838, 837, 840, 73/826, 831, 834, 835, 159; 254/228, 201; 69/19.1, 19.3

[56] References Cited

U.S. PATENT DOCUMENTS 2,864,582  12/1958  Hall .................................... 254/228

Primary Examiner—Jerry W. Myracle
Attorney, Agent, or Firm—Merriam, Marshall & Bicknell

[57] ABSTRACT

A portable seam tester is provided for testing the seam strength, on the job site, of large sections of flexible sheet material formed by seaming together smaller size panels. The tester has a piston and cylinder mechanism carrying spaced toggle action clamping means adapted to receive and retain folded double-thickness portions of the material at opposite sides of a seam. Pressurized fluid is controllably supplied to the cylinder to force the clamping means away from each other, thereby placing the material in tension so as to impose a predetermined stress on the seam.

10 Claims, 4 Drawing Figures

SEAM TESTER

This invention relates to a seam testing device that is especially adapted for use on large sections of flexible sheet material.

Large sections of flexible sheet material are often formed by seaming together smaller panels of the material. For example, ponds and reservoirs are often provided with flexible membrane liners of organic plastic or rubber-like sheet material in order to prevent ground water contamination of the contents of the pond or to safely contain harmful wastes. The liner is assembled from smaller size panels by seaming the panels on the job site using, for example, solvent or heat seaming techniques. It is necessary to test the strength of the finished seams so as to insure that the tensile strength requirements for the liner have been met. The usual test methods and apparatus for tensile testing are designed to be used in the laboratory with relatively small disposable samples of the material being tested and are not readily adapted for use in the field on large sections of flexible sheet material.

Accordingly, the primary object of the present invention is to provide a simple and relatively inexpensive portable device that is capable of convenient use in the field for testing the seam strength of large sections of flexible sheet material formed by seaming together smaller size panels of the material.

Other objects and advantages of the invention will become apparent from the subsequent detailed description in conjunction with the accompanying drawings, wherein.

Figure 1:
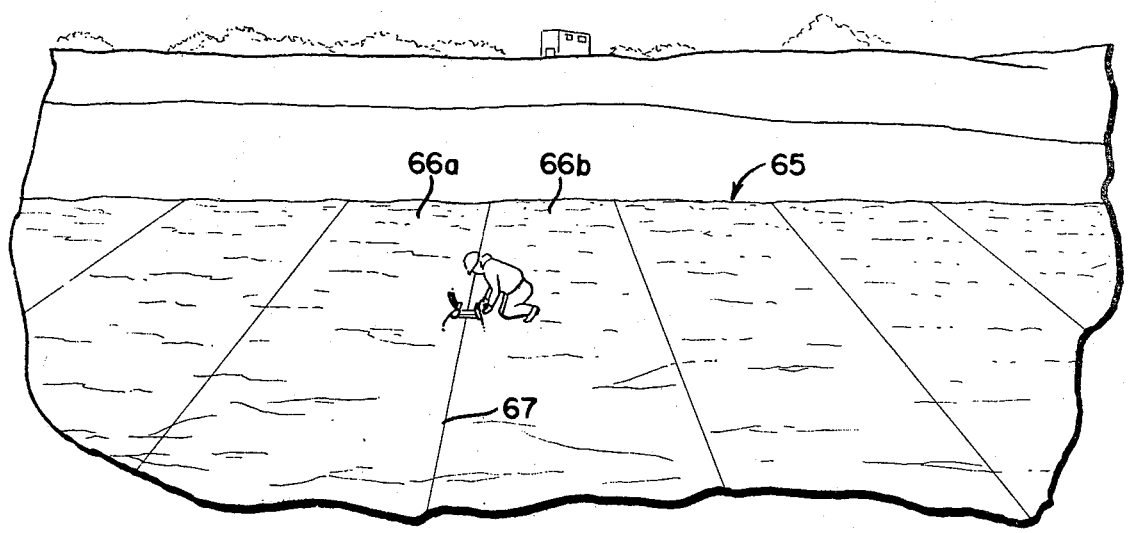
FIG. 1 is a generally schematic perspective view showing the manner in which the invention is used in the field to test a seam at an inner portion of a large pond liner.

The seam tester of the present invention comprises a hydraulic piston and cylinder mechanism designated generally at 10 and including an elongated cylinder 11 having a cupshaped cap or closure 12 at one end. A piston 13 is reciprocably disposed within the cylinder 11, and an elongated piston rod 14 is affixed at its inner end to the piston 13 and projects at its opposite end through an opening in the opposite end wall 15 of the cylinder 11. A clamping means designated generally at 16 is secured to the end closure 12 of the cylinder 11, as by a mounting stub 17, and a similar clamping means 16′ is carried at the outer end of the piston rod 14. As described below, the clamping means 16 and 16′ are adapted to engage and retain portions of the flexible sheet material being tested.

Figure 2:
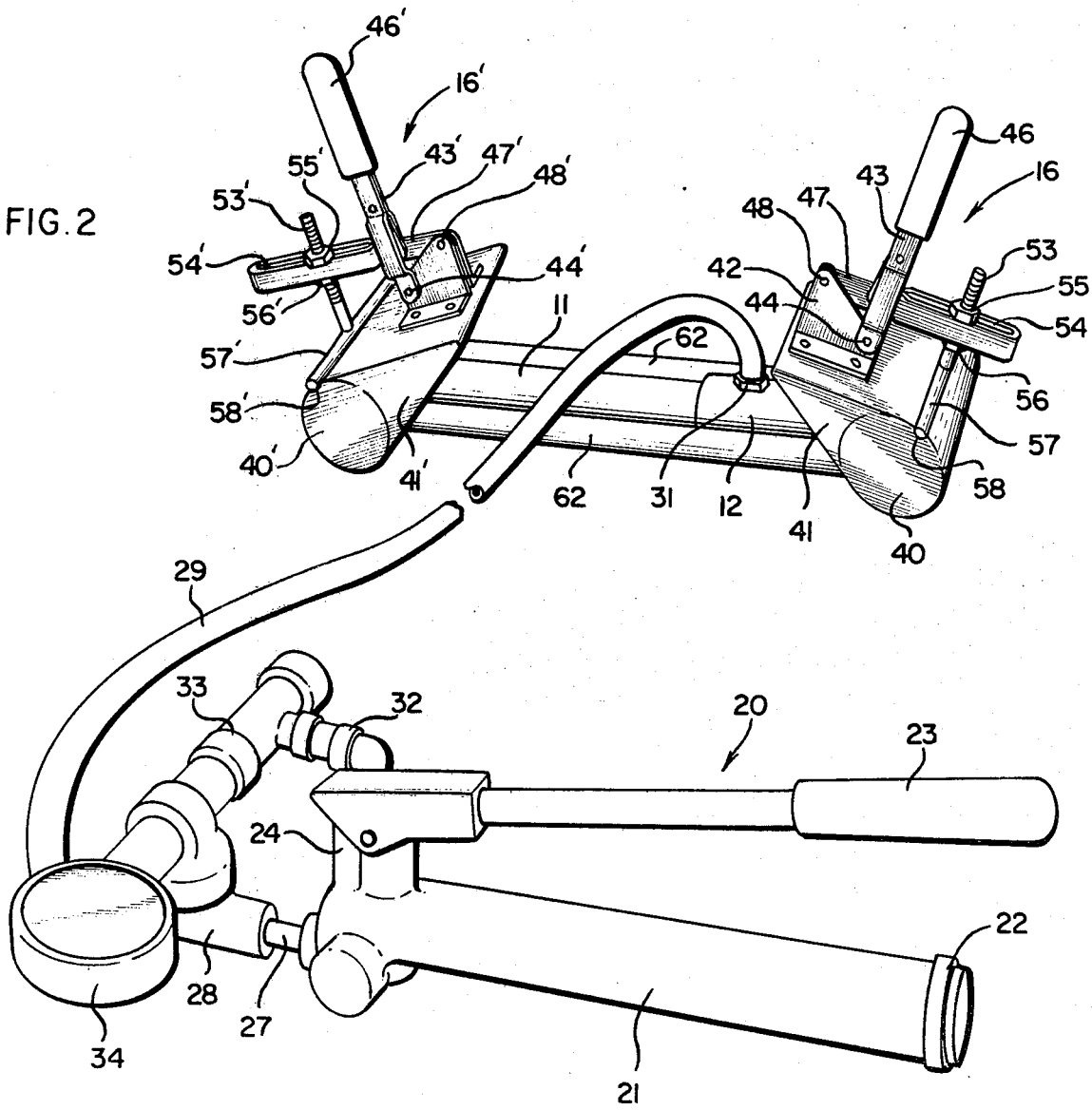
FIG. 2 is a perspective view of a seam testing device comprising one specific embodiment of the invention.

A hydraulic hand pump designated generally at 20 (FIG. 2) is provided for causing the piston 13 to move outwardly in the cylinder 11 from a retracted position to an extended position, thereby urging the clamping means 16 and 16′ away from each other to impose tension on the portion of the sheet material retained between the clamping means. The pump 20 has a barrel 21 containing hydraulic fluid and closed at one end by a cap 22. A manual pump lever 23 is pivotally mounted at the other end 24 of the barrel 21 and is connected to a plunger (not shown) that extends into the barrel 21 for pressurizing the hydraulic fluid which is thereby forced through an outlet 27, a fitting 28, and a flexible high pressure hose 29 connecting the fitting 28 with an inlet connector 31 secured to the closure 12 and the side wall of the cylinder 11. A pressure relief or by-pass line 32 connects the barrel 21 with an adjustable pressure relief valve 33 mounted on the fitting 28. A pressure gauge 34 is also mounted on the fitting 28. By adjustment of the pressure relief valve 33, the pressure of the hydraulic fluid supplied to the cylinder 11 can be controlled at a desired level.

The clamping means 16 and 16′ are essentially the same in construction and operation although arranged for opposite directions of movement. For convenience, only the right-hand clamping means 16 will be described in detail. Thus, the clamping means 16 comprises a generally cylindrical support or clamping drum 40 that is welded or otherwise rigidly secured to the stub 17 which is secured to the end closure 12. An integral extension or shelf 41 projects generally radially from the drum 40 and is inclined at an inward angle relative to the longitudinal axis of the piston and cylinder mechanism 10. An upright bracket 42 is affixed to the upper flat surface of the extension 41 for mounting a manually operable toggle linkage. The toggle linkage comprises a hand lever 43 having its lower end pivotally connected at 44 to the bracket 42 and having a hand grip portion 46 at its upper end. Another lever 47 has an inner end pivotally connected at 48 to the bracket 42, the axis of the pivot connection 48 being laterally spaced from and elevated in relation to the axis of the pivot connection 44 for the hand lever 43. A short link 49 has its ends pivotally connected at 51 and 52 to intermediate portions of the levers 43 and 47, respectively.

Figure 3:
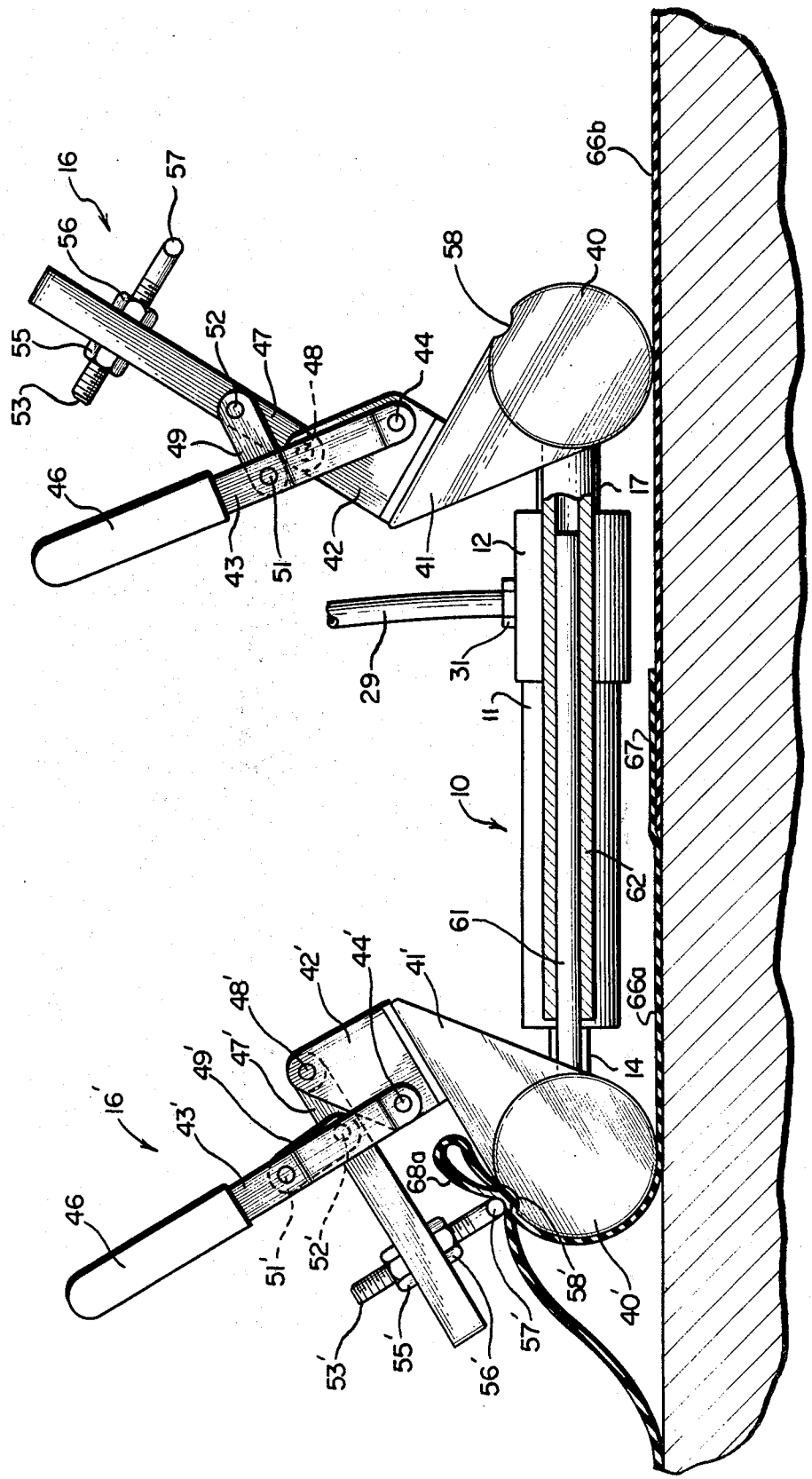
FIG. 3 is a side elevational view, partially in section, of the device of FIG. 2 showing the manner in which the liner is secured to the device when it is in its retracted position.

A rod 53 has a threaded end portion that extends through an elongated slot 54 (FIG. 2) in the outer end portion of the lever 47, and the rod 53 is secured in any desired adjusted position on the lever 47 by means of a pair of nuts 55 and 56 mounted on the threaded portion of the rod 53 and engaging opposite sides of the lever 47 bridging the slot 54. Thus, the position of the rod 53 can be adjusted both longitudinally and transversely of the lever 47. The opposite end of the rod 53 has rigidly affixed to it an elongated transversely extending clamping bar 57 that is adapted to be swung into clamping position overlying a complementary axially extending groove or notch 58 formed in the outer surface of the drum 40. As best seen in FIG. 3, the surface of the groove 58 preferably has a concave curvature and the bar 57 has a circular cross-section, the radius of curvature of the groove 58 being somewhat greater than the radius of the bar 57 in order to facilitate the clamping action, as described below.

In order to prevent rotary displacement of the clamping means 16 and 16′ relative to the longitudinal axis of the piston and cylinder mechanism 10, the clamping means 16 and 16′ are interconnected by suitable guide means that can accomodate extension and retraction of the piston and cylinder. In the illustrated embodiment of the invention, the guide means comprises a pair of elongated rod members 61 extending rigidly from the drum 40′ of the clamping means 16′ along opposite sides of the piston and cylinder mechanism 10. The rods 61 are slidably and telescopically received in a pair of elongated tubular members 62 extending rigidly from the drum 40 of the clamping means 16. Thus, the relative orientation between the clamping means and the piston and cylinder mechanism is maintained while accomodating movement of the piston and cylinder mechanism between its extended and retracted positions.

Figure 4:
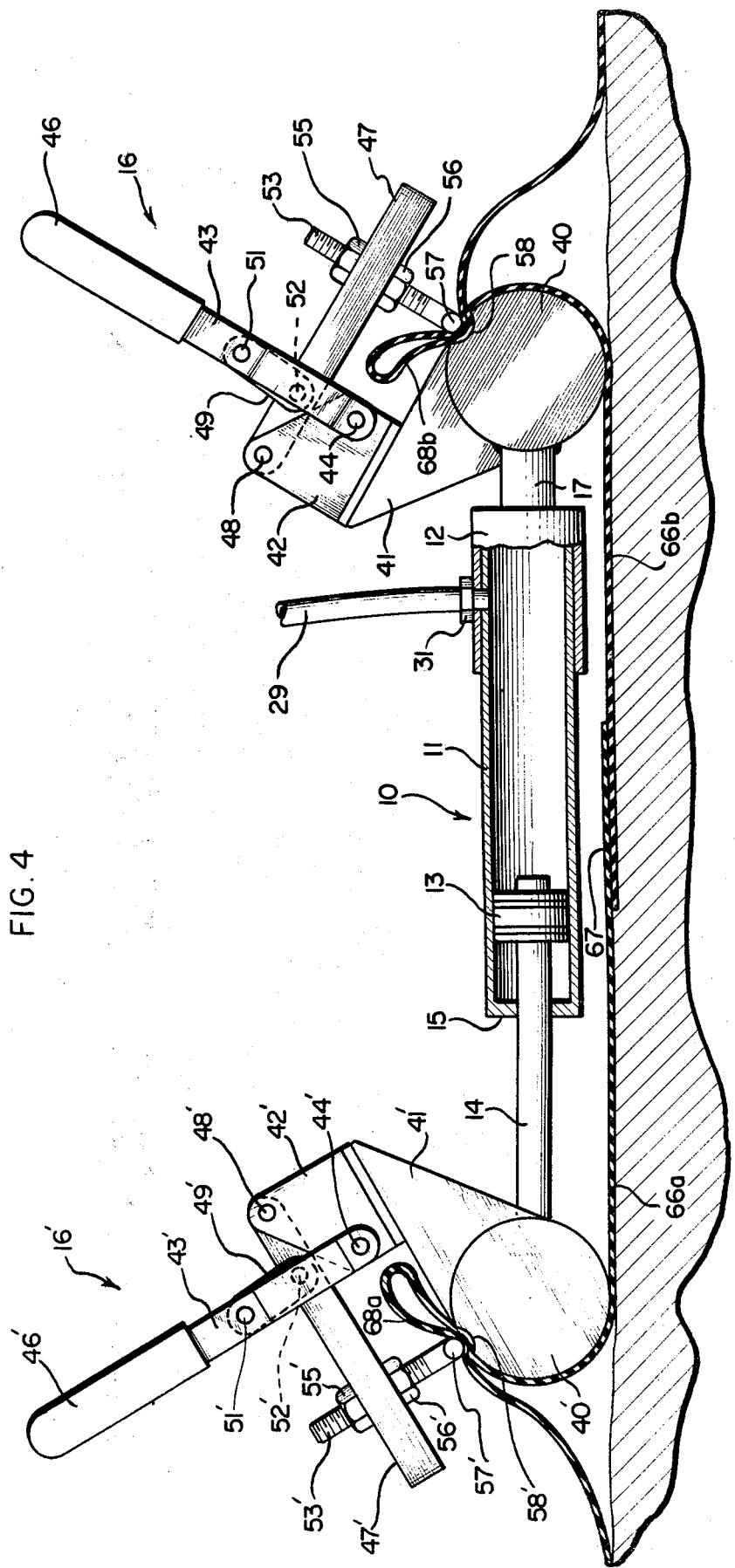
FIG. 4 is a view similar to FIG. 3 but with portions omitted for clarity and showing the device in its extended position during testing.

When the hand lever 43 is pivoted to the left, as seen in FIG. 3, the clamping means 16 is in its fully released position, but when the hand lever 43 is pivoted to the right, as shown in FIG. 4, the clamping bar 57 is swung in an arcuate path to its clamping position wherein a folded double-thickness portion of the flexible sheet material being tested is pressed into the groove 58 by the bar 57 and is frictionally retained therebetween. As will be understood from FIGS. 3 and 4, as the hand lever 43 is moved from its released position (FIG. 3) to its clamping position (FIG. 4), the pivot connections 51 and 52 of the link 49 move in arcuate paths until the pivot connection 51 is in its uppermost position and the pivot connection 52 is in its lowermost position and is also slightly overcenter relative to a line between the pivot axis 51 and the pivot axis 44. Thus, the toggle linkage retains the clamping bar 57 in clamping position until manually released.

In use in the field, the device may be disposed at any desired portion of a large pond liner or the like. As seen in FIG. 1, the device is disposed at an internal portion of a pond liner 65 inwardly of the periphery of the liner, the latter being assembled by seaming together a plurality of elongated discrete panels as designated at 66a and 66b. With the hand pump 20 depressurized and the piston and cylinder mechanism 10 in retracted position, the mechanism 10 is manually positioned transversely across an elongated overlapping seam 67 connecting the panels 66a and 66b, as in FIG. 3. The clamping means 16 and 16' are disposed at opposite sides of the seam 67. With the hand lever 43' in released position, the operator then pinches and lifts up the liner panel 66a adjacent the outer side of the clamping drum 40' and wraps the liner material upwardly and inwardly around the curved outer surface of the drum 40' until a folded double-thickness portion 68a of the liner material overlies and substantially overlaps the groove 58'. The grooves 58 and 58' are circumferentially located on the peripheries of the drums 40 and 40' so that the liner material is wrapped around more than 90° of the external curved surface of the drum and preferably at least about 135°. The hand lever 43' is then swung to its clamping position in which the clamping bar 57' engages the folded double-thickness portion 68a of liner material and forces it into the groove 58' so that the material is pressed against the drum 40' and frictionally retained.

The operation is repeated at the clamping means 16 so that a folded double-thickness portion 68b of the liner panel 66b is clamped between the drum 40 and the clamping bar 57, as seen in FIG. 4. By operating the hand pump 20, the piston and cylinder mechanism 10 is then extended and the clamping means 16 and 16' are moved away from each other whereby to place the liner material in tension transversely of the seam 67 and thereby impose a predetermined stress on the seam. As will be understood, the device can easily be moved to other areas of the liner and the test procedure repeated any desired number of times without the necessity of removing samples of the seamed material for destructive testing.

By adjustment of the position of the rods 53, 53' on the levers 47, 47', the clamping pressure between the bars 57, 57' and the drums 40, 40' can be regulated to accomodate varying thickness of the flexible sheet material and to achieve a desired clamping pressure.

Although the invention has been described with reference to a specific structural embodiment, it is to be understood that other modifications and equivalents may be resorted to without departing from the scope of the invention as defined in the appended claims.

We claim:

1. A portable seam tester for use on a large section of flexible sheet material formed from smaller panels of said material secured together along elongated seams, said tester comprising:
   an elongated piston and cylinder mechanism having a retracted position and an extended position;
   a pair of clamping means carried on said piston and cylinder mechanism;
   said tester being adapted to be positioned transversely across a seam of said large section of flexible sheet material inwardly from the periphery of said section with said clamping means disposed at opposite sides of the seam, and said clamping means being adapted to receive and retain folded double-thickness portions of said material at opposite sides of the seam when said piston and cylinder mechanism is in said retracted position;
   each of said clamping means comprising a support having a curved outer surface portion adapted to have said material wrapped therearound, and a manually operable clamping member mounted on said support and being movable from a released position to a clamping position in which said clamping member presses said folded double-thickness portion of said material against the outer surface of said support for frictionally retaining said material; and
   means for controllably supplying pressurized fluid to said piston and cylinder mechanism to effect movement thereof toward said extended position, whereby to place said material in tension and impose a predetermined stress on the seam.

2. The device of claim 1 wherein said piston and cylinder mechanism comprises an elongated cylinder, a piston reciprocably disposed in said cylinder, and an elongated piston rod extending into one end of said cylinder and having an inner end affixed to said piston; said clamping means being mounted at the outer end of said piston rod and at the opposite end of said cylinder.

3. The device of claim 1 wherein said support comprises a generally cylindrical drum with an axially extending groove in its outer surface, and said clamping member comprises an elongated bar adapted to press said portion of said material into said groove when in said clamping position.

4. The device of claims 1 or 3 wherein said clamping means includes a manually operable toggle linkage pivotally connected to said support, and said clamping member is adjustably mounted on said toggle linkage for accomodating varying thickness of said material and regulating the clamping pressure.

5. The device of claim 1 wherein elongated guide means extends between said clamping means for maintaining the relative orientation of said clamping means and said piston and cylinder mechanism while accomodating movement of said mechanism between its extended and retracted positions.

6. The device of claim 5 wherein said guide means comprises a pair of elongated tubular members extending rigidly from one of said clamping means along opposite sides of said piston and cylinder mechanism and a pair of elongated rod members extending rigidly from the other of said clamping means and telescopically received in said tubular members.

7. A portable seam tester for use on a large section of flexible sheet material formed from smaller panels of said material secured together along elongated seams, said tester comprising:

an elongated piston and cylinder mechanism having a retracted position and an extended position;

a pair of clamping means carried opposite said piston and cylinder mechanism;

elongated guide means extending between said clamping means for preventing rotary displacement of said clamping means relative to the longitudinal axis of said piston and cylinder mechanism;

said tester being adapted to be positioned transversely across a seam of said large section of flexible sheet material inwardly from the periphery of said section with said clamping means disposed at opposite sides of the seam;

each of said clamping means comprising a support having a curved outer surface portion adapted to have said material wrapped therearound, a manually operable toggle linkage pivotally mounted on said support, and a clamping member carried by said toggle linkage, said toggle linkage being movable from a released position to a clamping position in which said clamping member presses a folded double-thickness portion of said material against the outer surface of said support for frictionally retaining said material; and means for controllably supplying pressurized fluid to said piston and cylinder mechanism to effect movement thereof toward said extended position, whereby to place said material in tension and impose a predetermined stress on the seam.

8. The device of claim 7 wherein said support comprises a generally cylindrical drum with an axially extending groove in its outer surface, and said clamping member comprises an elongated bar adapted to press said portion of said material into said groove when in said clamping position.

9. The device of claim 7 wherein said clamping member is adjustably mounted on said toggle linkage for accomodating varying thickness of said material and regulating the clamping pressure.

10. The device of claim 7 wherein said guide means comprises a pair of elongated tubular members extending rigidly from one of said clamping means along opposite sides of said piston and cylinder mechanism and a pair of elongated rod members extending rigidly from the other of said clamping means and telescopically received in said tubular members.

* * * * *